United States Patent [19]

Crocker et al.

[11] Patent Number: 5,295,962
[45] Date of Patent: Mar. 22, 1994

[54] DRUG DELIVERY AND DILATATION CATHETER

[75] Inventors: Michael D. Crocker, Mission Viejo; Michael R. Henson, Pleasonton; Muny Chum, Santa Ana, all of Calif.

[73] Assignee: Cardiovascular Dynamics, Inc., Irvine, Calif.

[21] Appl. No.: 992,835

[22] Filed: Dec. 18, 1992

Related U.S. Application Data

[63] Continuation-in-part of Ser. No. 875,966, Apr. 29, 1992.

[51] Int. Cl.⁵ .................................... A61M 29/00
[52] U.S. Cl. ................................. 604/101; 604/96; 606/194
[58] Field of Search .................. 604/53, 96, 101; 606/192, 194

[56] References Cited

U.S. PATENT DOCUMENTS

| | | |
|---|---|---|
| 2,930,377 | 3/1960 | Cowley . |
| 3,173,418 | 3/1965 | Baran . |
| 3,435,824 | 4/1969 | Gamponia . |
| 3,769,981 | 11/1973 | McWhorter . |
| 3,889,685 | 6/1975 | Miller, Jr. et al. . |
| 3,889,686 | 6/1975 | Duturbure . |
| 4,195,637 | 4/1980 | Gruntzig et al. . |
| 4,198,981 | 4/1980 | Sinnreich . |
| 4,230,119 | 10/1980 | Blum . |
| 4,329,993 | 5/1982 | Lieber et al. . |
| 4,417,576 | 11/1983 | Baran . |
| 4,423,725 | 1/1984 | Baran et al. . |
| 4,447,227 | 5/1984 | Kotsanis . |
| 4,581,017 | 4/1986 | Sahota . |
| 4,597,755 | 7/1986 | Samson et al. . |
| 4,636,195 | 1/1987 | Wolinsky . |
| 4,646,742 | 3/1987 | Parkard et al. . |
| 4,661,094 | 4/1987 | Simpson . |
| 4,693,243 | 9/1987 | Buras . |
| 4,744,366 | 5/1988 | Jang . |
| 4,748,981 | 6/1988 | Crittenden . |
| 4,748,982 | 6/1988 | Horzewski et al. . |
| 4,762,129 | 8/1988 | Bonzel . |
| 4,763,654 | 8/1988 | Jang . |
| 4,771,777 | 9/1988 | Horzewski et al. . |
| 4,787,388 | 11/1988 | Hofmann . |
| 4,790,315 | 12/1988 | Mueller, Jr. et al. . |
| 4,795,427 | 1/1989 | Helzel . |
| 4,820,271 | 4/1989 | Deutsch . |
| 4,832,028 | 5/1989 | Patel . |
| 4,877,031 | 10/1989 | Conway et al. . |
| 4,892,519 | 1/1990 | Songer et al. . |
| 4,909,252 | 3/1990 | Goldberger et al. . |
| 4,944,745 | 7/1990 | Sogard et al. . |
| 4,968,306 | 11/1990 | Huss et al. . |
| 4,968,307 | 11/1990 | Dake et al. . |
| 4,994,033 | 2/1991 | Shockey et al. . |
| 5,049,132 | 9/1991 | Shaffer et al. . |
| 5,087,244 | 2/1992 | Wolinsky et al. . |
| 5,098,381 | 3/1992 | Schneider ........................ 604/96 |
| 5,112,305 | 5/1992 | Barath et al. .................... 604/96 |
| 5,176,638 | 1/1993 | Don Michael .................. 604/101 |
| 5,199,951 | 4/1993 | Spears ............................. 604/96 |
| 5,213,576 | 5/1983 | Abiuso et al. ................... 604/96 |

FOREIGN PATENT DOCUMENTS

| | | |
|---|---|---|
| 8912478 | 12/1989 | World Int. Prop. O. . |
| 9211895 | 7/1992 | World Int. Prop. O. .......... 604/101 |

*Primary Examiner*—C. Fred Rosenbaum
*Assistant Examiner*—Corrine Maglione
*Attorney, Agent, or Firm*—Knobbe, Martens, Olson & Bear

[57] ABSTRACT

An improved drug delivery catheter, for use in the prevention of restenosis of a dilated vascular region, and/or for use in the delivery of a medication to a preselected vascular site. The catheter comprises an elongate body, an inflation balloon disposed about a catheter body. In a drug delivery embodiment, a perforated drug delivery balloon is disposed concentrically about the inflation balloon. In another embodiment, the two balloons are heat sealed together at the distal and proximal ends of the catheter body. A first lumen extends through the catheter body for communicating with the inflation balloon, and a second lumen extends through the body for communicating with the drug delivery balloon. Methods describing the intraluminal delivery of drugs to a site specific location are also disclosed, including the delivery of a drug to a vascular area before, during or after a conventional PTCA procedure.

23 Claims, 5 Drawing Sheets

DRUG DELIVERY AND DILATATION CATHETER

RELATED APPLICATIONS

This application is a continuation-in-part of application Ser. No. 875,966 filed on Apr. 29, 1992 pending.

BACKGROUND OF THE INVENTION

The present invention relates to catheters for insertion into a body lumen. More particularly, the present invention relates to a drug delivery catheter for use in the vascular system.

A wide variety of catheters have been developed in the prior art for percutaneous transluminal coronary or peripheral vascular applications. For example, balloon dilatation catheters for performing percutaneous transluminal coronary angioplasty are well known in the art.

In addition, a variety of catheters have been developed in the prior art for delivering therapeutic agents into the vascular system. For example, U.S. Pat. No. 4,636,195 to Wolinsky discloses the isolation of an arterial plaque between two ring balloons, and introduction of a solubilizing liquid therebetween. U.S. Pat. No. 5,049,132 to Shaffer et al. discloses an over the wire type catheter having an inner dilatation balloon disposed within an outer perforated drug delivery balloon. Similarly, U.S. Pat. No. 4,994,033 to Shockey et al. discloses concentric inner dilatation and outer delivery balloons disposed coaxially about an over the wire catheter.

In connection with other applications, U.S. Pat. Nos. 3,173,418 and 4,417,576 to Baran disclose double walled endotracheal cuffs having an external wall with multiple perforations for the administration of continuous or intermittent local endotracheal anesthesia. Fluid communication to the balloons is provided by way of fluid tubes which may be positioned within the endotracheal cuff wall.

In addition, a variety of patents appear to address the problem of inadequate perfusion associated with balloon dilatation angioplasty catheters, during the period of time that the balloon is inflated. For example, U.S. Pat. Nos. 4,877,031 to Conway et al. and 4,892,519 to Songer et al. disclose conventional balloon dilatation catheter designs, without any apparent drug delivery capability, in which a relatively low volume perfusion conduit is provided.

Finally, U.S. Pat. No. 4,423,725 to Baran et al. purports to disclose a combination dilatation and drug delivery design having a means for continued perfusion across the dilated balloon. Although stated to be useful in angioplasty, the catheter is also designed for use in tracheal, bladder and urethral treatments. If the Baran design were scaled down to an appropriate size for angioplasty use, only minimal perfusion would appear to be permitted by way of a plurality of side ports which communicate with the guide wire lumen.

Several of the catheters discussed above which have been approved by the FDA use a bolus method to deliver a liquid medication through an end hole or multiple side holes of the catheter. This method provides a mass delivery of the drug near the area of interest, and relies on the washing of the drug down the artery to deliver the drug to the desired location.

Other catheters, such as the one described in U.S. Pat. No. 5,087,244 to Wolinsky utilize a high pressure fluid delivery system which causes the drug to penetrate through the layers of the luminal wall beyond the artery's internal elastic lamina, referred to as intramural drug delivery.

Notwithstanding the foregoing, there remains a need for a drug delivery catheter, specially adapted for use in the relatively small diameter environments of the coronary and peripheral vascular systems. Optimally, the catheter will permit delivery of fluid medication to a site specific location in the vascular system or other body lumen.

SUMMARY OF THE INVENTION

There is disclosed in accordance with one aspect of the present invention, a delivery catheter for delivering a quantity of medication or other fluid treatment media to a preselected site in a body lumen. The drug delivery catheter comprises an elongate catheter body, having an inflation balloon on the distal end thereof. An infusion or delivery balloon is provided on the catheter, disposed adjacent to the inflation balloon. A first lumen extends through the catheter for communication with the inflation balloon, and second lumen extends through the catheter for communication with the infusion balloon. Preferably, the delivery balloon extends coaxially about the inflation balloon. More preferably, a portion of the proximal and a portion of the distal ends of the two balloons are heat sealed together as described infra.

Preferably, the delivery balloon includes a plurality of delivery ports 40 to deliver the fluid treatment to the site specific location. The deliver ports 40 are preferably between 100 $\mu$m and 300 $\mu$m in diameter, and more preferably 250 $\mu$m in diameter.

Another feature of the present invention further includes a wire receiving lumen extending throughout at least a portion of the axial length of the catheter body, for receiving a wire to improve pushability of the catheter.

Another feature of the present invention includes a method of intraluminal fluid delivery to a preselected vascular site utilizing a delivery catheter of the type having an elongate catheter body and at least one inflatable delivery balloon in communication with the proximal end of the catheter body by a delivery lumen. The catheter is positioned so that the balloon is adjacent a desired delivery site. The balloon is inflated to position the wall of the balloon adjacent the wall of the vascular site. Fluid is introduced into the balloon by way of the delivery lumen, so that fluid is caused to advance from the balloon to a site on the vascular wall. The balloon is thereafter deflated and removed from the vascular site.

Preferably, an inflation balloon is provided within the delivery balloon. In this embodiment, the deflation step is accomplished by excavating the inflation balloon thereby reducing the profile of the delivery balloon.

A further aspect of the present invention enables a fluid to be delivered to a preselected vascular site before, during or after a conventional percutaneous transluminal coronary angioplasty (PTCA) procedure.

Further features and advantages of the present invention will become apparent from the detailed description of preferred embodiments which follows, when considered together with the attached claims and drawings.

DETAILED DESCRIPTION OF PREFERRED EMBODIMENTS

Figure 1:
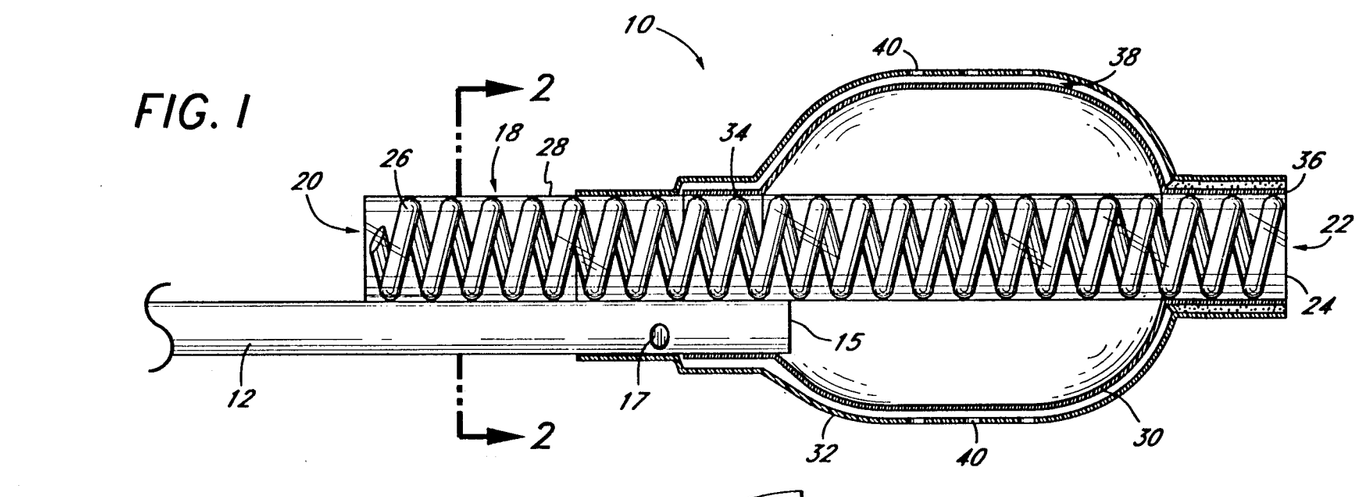
FIG. 1 is a partial sectional side elevational view of a drug delivery and temporary stent catheter in accordance with one aspect of the present invention.

Referring to FIG. 1, there is disclosed a combination drug delivery and temporary stent catheter in accordance with one aspect of the present invention. Although one embodiment of the present invention incorporates both the drug delivery and temporary stent features, catheters incorporating only a single of these features can also be readily produced in accordance with the disclosure herein, as will be appreciated by one of skill in the art. In addition, the catheter of the present invention can readily be used for angioplasty dilatation as well.

The catheter 10 generally comprises an elongate tubular body 12 for extending between a proximal control end (not illustrated) and a distal functional end. Tubular body 12 may be produced in accordance with any of a variety of known techniques for manufacturing balloon tipped catheter bodies, such as by extrusion of appropriate biocompatible plastic materials. Alternatively, at least a portion or all of the length of tubular body 12 may comprise a spring coil, solid walled hypodermic needle tubing, or braided reinforced wall as is well understood in the catheter and guidewire arts.

In general, tubular body 12, in accordance with the present invention, has a generally circular cross-sectional configuration having an external diameter within the range of from about 0.030 inches to about 0.065 inches. Alternatively, a generally triangular cross sectional configuration can also be used, with the maximum base to apex distance also within the range of from about 0.030 inches to about 0.065 inches. Other non circular configurations such as rectangular or oval may also be used. In peripheral vascular applications, the body 12 will typically have an outside diameter within the range of from about 0.039 inches to about 0.065 inches. In coronary vascular applications, the body 12 will typically have an outside diameter within the range of from about 0.030 inches to about 0.045 inches.

Diameters outside of the preferred ranges may also be used, provided that the functional consequences of the diameter are acceptable for a specified intended purpose of the catheter. For example, the lower limit of the diameter for tubular body 12 in a given application will be a function of the number of fluid or other functional lumen contained in the catheter, together with the acceptable flow rate of dilatation fluid or drugs to be delivered through the catheter.

In addition, tubular body 12 must have sufficient structural integrity (e.g., "pushability") to permit the catheter to be advanced to distal arterial locations without buckling or undesirable bending of the tubular body 12. The ability of the body 12 to transmit torque may also be desirable, such as in embodiments having a drug delivery capability on less than the entire circumference of the delivery balloon. Larger diameters generally have sufficient internal flow properties and structural integrity, but reduce perfusion in the artery in which the catheter is placed. In addition, increased diameter catheter bodies tend to exhibit reduced flexibility, which can be disadvantageous in applications requiring placement of the distal end of the catheter in a remote vascular location.

Figure 2:
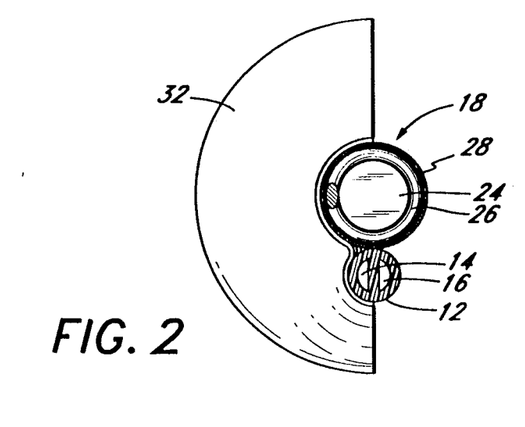
FIG. 2 is a cross sectional view taken along the lines 2—2 of FIG. 1.

As can best be seen by reference to FIG. 2, the tubular body 12, in accordance with the illustrated embodiment of the present invention, preferably comprises at least a first lumen 14 and a second lumen 16 extending axially therethrough. Inflation lumen 14 is in fluid communication with the interior of inflation balloon 30 by way of port 15. Drug delivery lumen 16 is in fluid communication with a drug delivery balloon 32 by way of port 17. In this manner, inflation fluid or fluid medication can be selectively introduced into the inflation balloon 30 and drug delivery balloon 32, as will be described in greater detail infra.

Additional lumen can readily be formed in tubular body 12 by techniques known in the art. In one embodiment of the present invention (not illustrated), a third lumen is provided having an opening at its proximal end and a closed distal end. This third lumen receives a wire to improve pushability of the catheter. A further embodiment, illustrated in FIG. 5 and discussed infra, is provided with a guidewire lumen for over-the-wire manipulation.

In an alternate embodiment of the catheter body, two or more lumens are disposed in a concentric arrangement. See FIGS. 3 and 4. Tubular body 12 comprises an outer tubular wall 42 defining a first lumen 44 for communicating a fluid to the distal end of the catheter. An inner tubular wall 46 defines a second lumen 48. In the illustrated embodiment, inner lumen 48 is in fluid communication with the inflation balloon 30, and outer lumen 44 is in fluid communication with the drug delivery balloon 32. Concentric lumen catheter bodies can be manufactured in accordance with techniques known in the art.

A temporary stent 18 is secured to the distal end of tubular body 12. As illustrated in FIG. 1, the longitudinal axis of temporary stent 18 is laterally displaced from the longitudinal axis of tubular body 12. Stent 18 generally comprises a first end 20, a second end 22 and a lumen 24 extending therebetween (See FIG. 2). Blood flow through lumen 24 can occur in either direction, depending upon the location of percutaneous insertion and the direction of transluminal travel of the catheter.

In general, it is desired that the ratio of the interior cross-sectional area of lumen 24 to the maximum exterior cross-sectional area of the deflated balloon be maximized in order to optimize perfusion across the inflation balloon 30 while inflation balloon 30 is inflated. Catheters embodying the present invention having a perfusion deflated profile of 0.055 inches or greater can be produced having an interior lumen 24 with an interior diameter of at least about 0.030 inches, and preferably about 0.039 inches or greater. This fits readily within the lumen of a guide catheter, which may have an internal diameter of about 0.072 inches. Alternatively, the diameter of lumen 24 can be reduced to as low as about 0.012 inches and still function as a guidewire conduit.

In one embodiment of the present invention, the interior diameter of lumen 24 is about 0.039 inches (1 mm). This lumen will typically provide a flow at 80 mm Hg of greater than 60 ml/minute. The coil wall thickness of about 0.002 inches adds 0.004 inches to the diameter of stent 18. The outer sheath 28, described infra, has a thickness of about 0.001 inches and produces an assembled stent 18 having an outside diameter of about 0.045 inches.

The design of the present invention provides a significant passageway 24 cross sectional area compared to the overall cross sectional area of stent 18. This parameter is important because only the stent 18 and balloon will typically traverse the stenotic site. The distal end of catheter body 12 (i.e., port 15) typically ends proximally of the stenosis in the preferred application.

This parameter is conveniently expressed in terms of the percentage of the outside diameter of stent 18 that the thickness of a single wall of stent 18 represents. In other words, in a preferred embodiment, a 0.003 inch wall thickness is about 6.7% of the 0.045 inch outside diameter.

Preferably, this percentage is less than about 14%, more preferably less than about 8%, and most preferably less than about 5% to optimized perfusion through the inflated balloon. Lower percentages may be achievable through the use of new materials or techniques not yet developed.

Lower percentages can be obtained by sacrificing pushability or by development or use of new high strength materials. For example, if sufficiently structurally sound for a given application, use of a 0.002 inch stent wall in a 0.045 inch diameter catheter will produce a 4.4% value. In addition, the percentage can be reduced by increasing the outside diameter of the stent to the maximum permitted for a given application.

Temporary stent 18 preferably comprises a support structure for resisting radial compression of passageway 24 by the inflated balloon 30. Suitable support structures include braided or woven polymeric or metal reinforcement filaments or a spring coil 26. Spring coil 26 preferably comprises a material having suitable biocompatability and physical properties, such as a stainless steel or platinum wire. Alternatively, polymeric materials such as nylon or Kevlar (DuPont) may also be used. Preferably, rectangular ribbon is used, having cross-sectional dimensions on the order of about 0.001 inches by about 0.003 inches for small vessels, and on the order of about 0.005 inches by about 0.010 inches for use in larger vessels.

The wire or ribbon is preferably wound to produce a coil having an interior diameter within the range of from about 0.030 inches (coronary) to about 0.100 inches (periphery) and an exterior diameter within the range of from about 0.032 inches (coronary) to about 0.110 inches (periphery).

Spring coil 26 may be either "tightly wound" so that adjacent loops of coils are normally in contact with each other, or "loosely wound," as illustrated in FIG. 1, in which the adjacent loops of coil are normally separated from one another. The selection of a tightly wound or loosely wound coil for use in the present invention will be influenced by such factors as the desired weight of the finished catheter, the relative flexibility of the catheter in the region of temporary stent 18, and the amount of radially inwardly directed compressive force exerted by the inflation balloon 30, as will be apparent to one of skill in the art. Radiopacity may also be a factor.

Preferably, spring coil 26 is provided with an outer sheath or coating 28. Sheath 28 may be produced by dipping, spraying, heat shrinking or extrusion techniques which are understood in the art, and preferably comprises a relatively flexible material having sufficient biocompatability to enable its use in contact with the vascular intima. Suitable materials for sheath 28 comprise linear low density polyethylene such as that produced by Dow, polyethylene terephthalate, nylons, polyester or other known or later developed medical grade polymers.

Figures 3, 4:
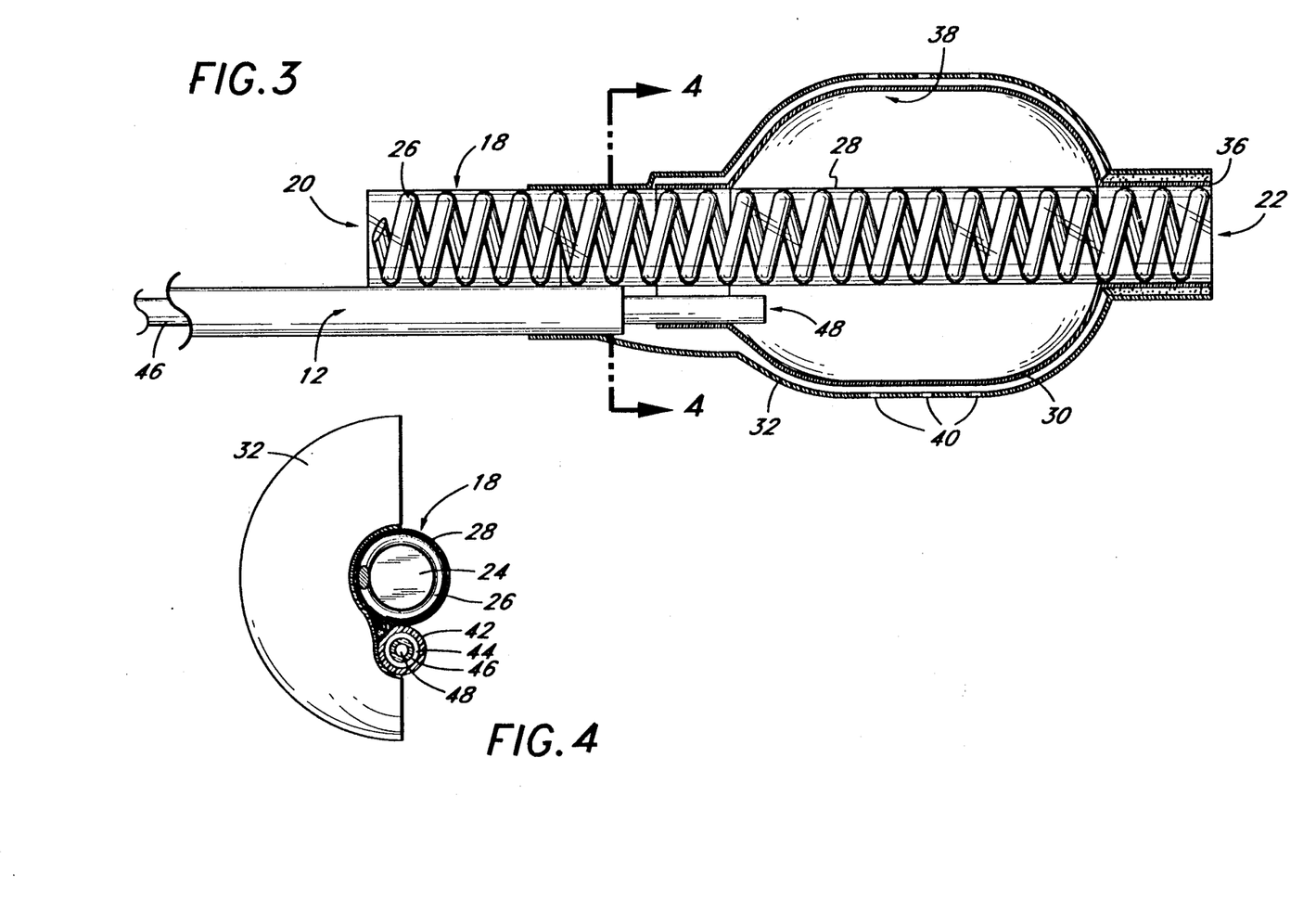
FIG. 3 is a partial sectional side elevational view of a second embodiment of the invention, having a coaxially configured catheter body.
FIG. 4 is a cross-sectional view taken along the lines 4—4 in FIG. 3.

Inflation balloon 30 generally comprises a proximal neck portion 34, a distal neck portion 36 and an intermediate dilatation portion 38. Referring to FIGS. 1 and 3, it can be seen that the proximal neck of each balloon is larger in diameter than the distal neck to accommodate the catheter body 12.

Proximal neck portion 34 is tightly secured to the temporary stent 18 and distal portion of tubular body 12, such as by the use of conventional adhesives, thermal bonding or heat shrinking techniques. The interstitial space formed by the diverging walls of tubular body 12 and temporary stent 18 (in a circular cross section embodiment) may be provided with a fluid-tight seal such as by filling with adhesive. In this manner, a fluid-tight seal between the proximal neck portion 34 and the elongate tubular body 12 and temporary stent 18 is provided.

The distal neck 36 of inflation balloon 30 is provided with a fluid-tight seal with the distal portion of temporary stent 18. This seal may also be accomplished in any of a variety of manners known in the art, such as by the use of heat shrink materials, adhesives, or other thermal bonding or solvent bonding techniques. Preferably, distal neck 36 of inflation balloon 30 is heat shrunk onto stent 18.

As will be appreciated by one of skill in the art, the sheath 28 cooperates with the dilatation portion 38 of the inflation balloon 30 to provide a sealed compartment for retaining a dilatation fluid therein.

In a preferred embodiment of the illustrated design, the inflation balloon comprises a relatively non-elastic material such as linear low density polyethylene, polyethyleneterephthalate, nylon, polyester, or any of a variety of other medical grade polymers known for this use in the art. Preferably, the geometry, material and seals of balloon 30 will withstand an internal pressure of at least about 5 ATM and, preferably, about 10 ATM without any leakage or rupture.

Balloon 30 is preferably premolded to have an inflated diameter in a catheter intended for peripheral vascular applications within the range of from about 1.5 mm to about 8 mm. The balloon 30 in a catheter intended for coronary vascular applications preferably has an inflated diameter range of from about 1.5 mm to about 4 mm.

Although the present invention has been described in terms of an "inflation" balloon 30, it is to be understood that the balloon 30 can also function as a dilatation balloon, such as is well known in the art of percutaneous transluminal coronary angioplasty and other applications in which dilatation of a stenotic region in a body lumen is desired. In an embodiment of the present invention in which dilatation properties are desired, conventional dilatation balloon materials and design considerations can readily be incorporated, as will be understood by one of skill in the art. Alternatively, if the inflation balloon 30 is merely desired to provide sufficient radially expansive force to compress the drug delivery balloon 32 against the wall of the vessel, considerations appropriate for a lower pressure system may be utilized.

The drug delivery balloon 32 is most conveniently disposed radially outwardly from the inflation balloon 30. Drug delivery balloon 32 may comprise a generally non-elastic material such as is conventional for angioplasty dilatation balloons, or may alternatively comprise an elastic material such as latex or urethane, or any other suitably biocompatible elastomer. Use of an elastic material for drug delivery balloon 32 can assist in reducing the relatively rough edges of the collapsed inflation balloon 30, and thereby reduce trauma to the vascular intima during insertion and withdrawal of the catheter.

Drug delivery balloon 32 is provided with a plurality of delivery ports 40. Delivery ports 40 may be disposed radially symmetrically about the outer periphery of the delivery balloon 32, or may be limited to only portions of the exterior surface of the delivery balloon 32, depending upon the desired drug delivery pattern. For example, delivery ports 40 can be positioned only on one hemisphere of balloon 32. Alternatively, delivery ports 40 can extend for less than the entire length of the balloon.

Delivery balloon 32 alternatively comprises a material which is inherently permeable, without the provision of discrete delivery ports 40. For example, woven or braided filaments or fabrics can be used. For relatively low delivery rate applications, fluid permeable membranes can also be used.

As can be seen with reference to FIG. 1, drug or other fluid introduced by way of lumen 16 is expressed by way of port 17 into the interior space of drug delivery balloon 32. The inflated volume of inflation balloon 30 causes the drug to be expelled by way of ports 40 outside of the drug delivery system.

Preferably, the relative inflated dimensions of the delivery balloon 32 and the inflation balloon 30 are such that a minimum amount of drug is retained between the two balloons. Thus, preferably, the inflated inflation balloon 30 substantially completely fills the interior chamber of drug delivery balloon 32 to efficiently expel essentially all of the fluid introduced into drug delivery balloon 32 by way of drug delivery lumen 16. Residual volume of drugs contained in lumen 16 can be expelled outside of the balloon such as by following the drug with a small volume of normal saline or other "rinse" solution, as will be understood by one of skill in the art.

In a further alternative, the inflation and drug delivery are accomplished by the same balloon. In this embodiment, the permeability rate of the balloon material, or the diameter and number of delivery ports 40 are sufficiently small that the balloon is sufficiently firmly inflated without delivery at an excessive rate. Appropriate permeability rates for the balloon material can be determined through routine experimentation, in view of such factors as the viscosity of the drug, desired delivery rate and the desired radially expansive force to be exerted by the balloon.

Figure 5:
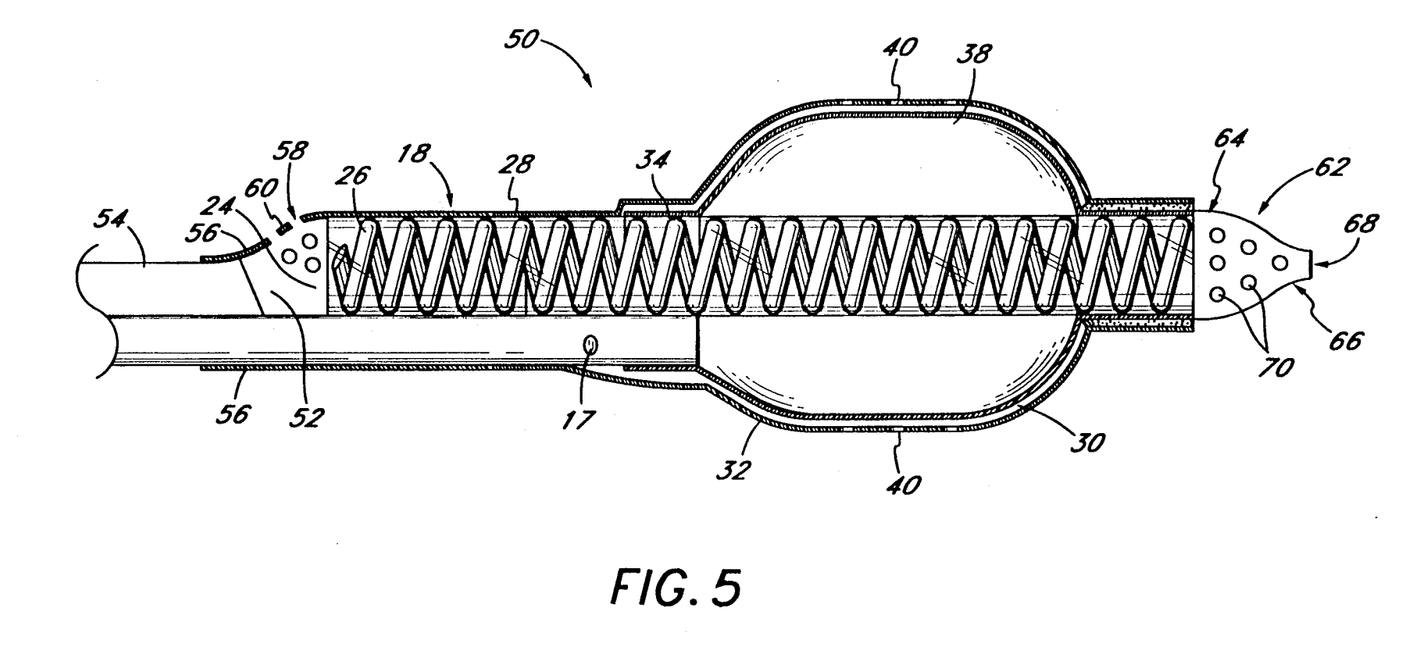
FIG. 5 is a partial sectional side elevational view of an over-the-wire embodiment of the present invention.
Figure 6:
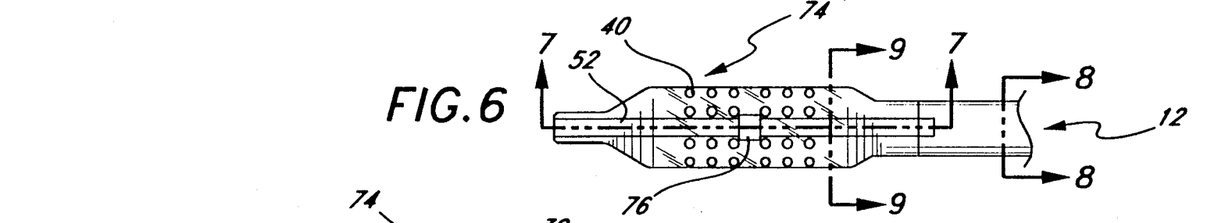
FIG. 6 is a partial sectional side elevational view of a non-stent embodiment of the present invention.

Referring to FIG. 5, there is disclosed an over-the-wire embodiment in accordance with the present invention. Over-the-wire catheter 50 is provided with a third lumen 52 extending through housing 54. In one embodiment, housing 54 comprises a separate tube which is secured along the outside of catheter body 12 such as by adhesives or other plastic bonding techniques known in the art. Preferably, however, housing 54 comprises an integrally formed three lumen catheter body as is well known in the art. Lumen 52 is provided with a sufficient interior cross-sectional area to axially slidably receive a conventional guidewire, such as a 0.014 inch guidewire.

In a preferred embodiment of the present invention, an extruded three lumen catheter body is prepared in accordance with techniques known in the art. One lumen, intended as guidewire lumen 52, has an internal diameter of at least about 0.016 inches. The wall surrounding lumen 52 is thereafter cut down using conventional cutting or grinding equipment. Alternatively, the catheter body is integrally molded with one lumen shorter that the other two, such as by injection molding about removable wire mandrels, and post molding cutting steps.

The distance between the distal end of lumen 52 and the proximal end of stent 18 can range from essentially zero up to an inch or more, particularly if a cover 60 is used as described infra. Preferably, however, the distance between the distal end of lumen 52 and the proximal end of stent 18 is no more than about 12 inches, and more preferably no more than about 0.2 inches.

In the embodiment illustrated in FIG. 5, the distal end of lumen 52 is about 0.08 inches from the proximal end of stent 18, and about 0.5 inches from port 15.

Preferably, a distal extension of the longitudinal axis of lumen 52 is aligned to extend through the lumen 24 in temporary stent 18. In this manner, a guidewire which is threaded distally through lumen 52 will thereafter be directed through lumen 24. This design facilitates removal and reinstallation of the guidewire while the catheter 50 is in place.

As an optional feature in accordance with the present invention, the proximal neck of one or both of the balloons 30, 32 extends in a proximal direction to form a seal 56 around housing 54. In this manner, a cover 60 is provided for the proximal end of lumen 24. Cover 60 can both assist in the withdrawal of the catheter from the vascular system, as well as assist in ensuring that a guidewire advanced distally through lumen 52 is guided into lumen 24. In an embodiment incorporating this feature, the cover 60 is provided with a plurality of perfusion ports 58 to permit continued perfusion through cover 60 and lumen 24. Preferably, the cover 60 comprises a proximal extension of delivery balloon 32.

As an additional optional feature in accordance with the present invention, there is provided a flexible, generally cone-shaped distal tip 62 for facilitating distal advancement of the catheter 50 along a previously positioned guidewire (not illustrated). Distal tip 62 comprises a relatively large diameter proximal portion 64 which is preferably an integral extension of either inflation balloon 30 or delivery balloon 32. Tip 62 tapers radially inwardly in a distal direction to a relatively narrow portion 66 having an axially-aligned guidewire and perfusion opening 68 therein.

The axial length of distal tip 62 may be varied depending upon a variety of factors such as the diameter and rigidly of the material used. In the preferred embodiment, distal tip 62 is made from the same material as delivery balloon 32, and may be formed by axially stretching the distal end of balloon 32 with the application of heat. The proximal port diameter is about 0.035 to 0.050 inches and the distal opening 68 in one embodiment has a diameter of about 0.016 inches. The axial length of tip 62 is about 0.4 inches.

To optimize perfusion through lumen 24, a plurality of ports 70 are distributed about the periphery of distal tip 62. Ports 70 in the preferred embodiment have a diameter of at least about 0.030 inches, and generally as many ports 70 (and ports 58) are provided as possible without unduly interfering with the structural integrity of the tip 62 (or cover 60). The precise configuration of distal tip 62 can be varied considerably, while still performing the function of providing a guide for the guidewire and permitting optimum perfusion through lumen 24.

Referring to FIGS. 6–10, there is disclosed a nonperfusion catheter embodiment 74 which also does not include a temporary stent. The non-perfusion embodiment 74 is preferably designed for use in percutaneous coronary transluminal angioplasty and adjunctive site specific intraluminal infusion of pharmacological agents.

The non-perfusion embodiment 74 preferably comprises a tubular body 12 which includes an inflation lumen 14, a drug delivery lumen 16, and a guidewire lumen 52. Two concentric balloons, an inner inflation balloon 30, and an outer delivery balloon 32 are connected to the tubular body 12. Alternatively, the inflation balloon and delivery balloon are disposed on opposing sides of the longitudinal axis of the body 12, such as for delivery of medication to an eccentric delivery site.

The inflation lumen 14 is in fluid communication with the inflation balloon 30 through port 15, the delivery lumen 16 is in fluid communication with the drug delivery balloon 32 through port 17, and the guidewire lumen 52 is in communication with a central lumen 75 which allows a guidewire to pass through the distal end of the catheter. A radiopaque marker 76 is preferably placed around the central lumen 75 in the center of the inflation balloon 32 to assist in positioning the catheter in the desired location. The tubular body 12 is preferably an integrally formed three lumen catheter body 78 as is well known in the art.

Figures 7, 8, 9, 10:
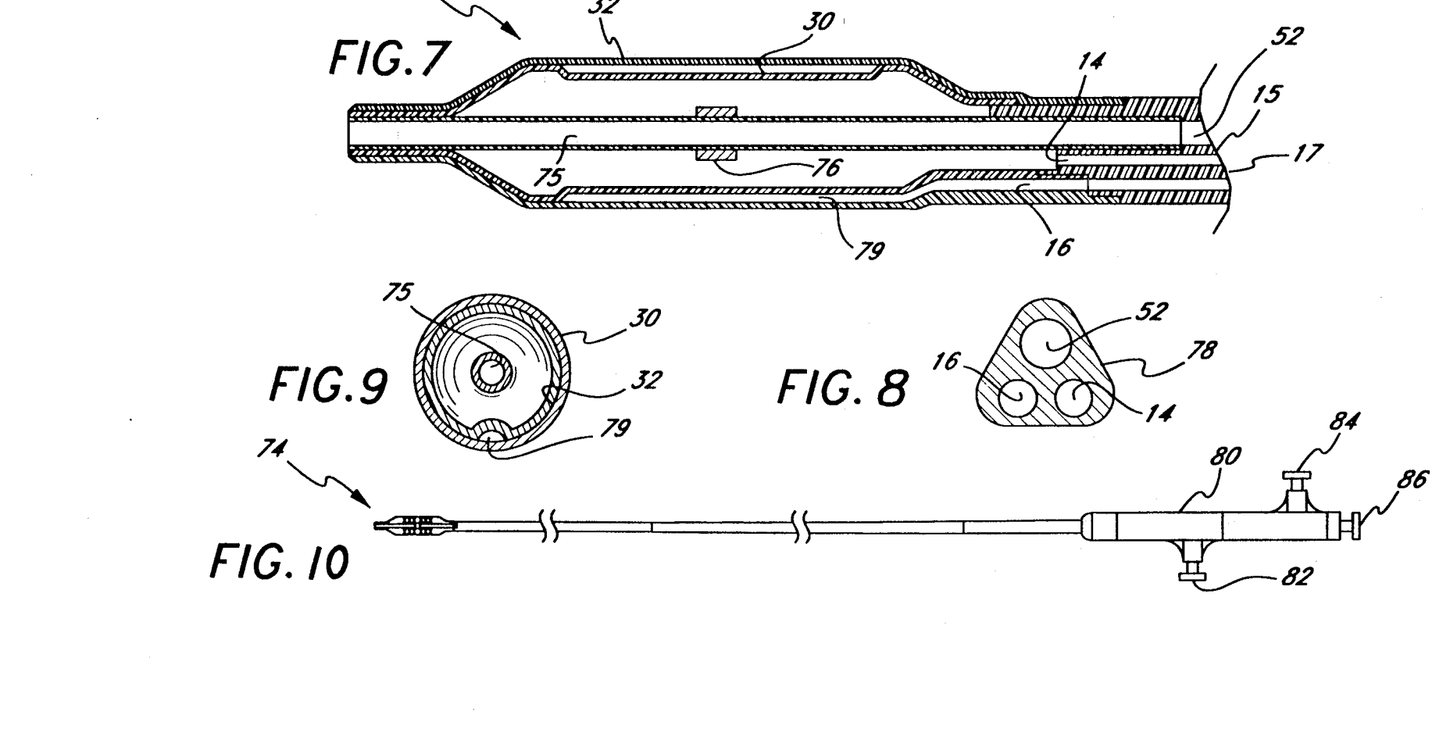
FIG. 7 is a cross-sectional view taken along the lines 7—7 in FIG. 6.
FIG. 8 is a cross-sectional view taken along the lines 8—8 in FIG. 6.
FIG. 9 is a cross-sectional view taken along the lines 9—9 in FIG. 6.
FIG. 10 is a side elevational view of a non-stent embodiment of the present invention in communication with a fluid delivery and guide-wire entry apparatus.

Preferably, the three lumen catheter body 78 has a triangular cross section for a majority of the length of the tubular body 12, as illustrated in FIG. 8. The triangular shape of the tubular body 12 provides a clearer fluoroscopy picture of the tubular body 12 within the patient, as the tubular shape reduces the cross sectional area of the tubular body 12 by up to 30%. The reduction in cross sectional area of the tubular body 12 thus allows for the injection of up to 30% more dye into the guiding tube (not shown) which provides a clearer fluoroscopy picture of the tubular body within the patient. Further, the reduction in cross sectional area of the tubular body 12 allows for more perfusion to occur around the catheter body 12.

Preferably, a distal extension of the longitudinal axis of the guide wire lumen 52 is aligned with a central lumen 75. In this manner, a guidewire which is threaded distally through lumen 52 will thereafter be directed through lumen 75. This design facilitates removal and reinstallation of the guidewire while the catheter 74 is in place.

As illustrated in FIG. 9, the central lumen 75 is typically concentric with both the inflation balloon 30 and delivery balloon 32 and extends through the center of the inflation balloon 30 and exits out the distal end of the catheter. The delivery lumen 16 extends into the catheter body and is in fluid communication with the delivery balloon 32. As described infra, during infusion of a fluid into the delivery balloon a small luminal channel 79 is maintained between the inflation and delivery balloons 30, 32 to enable the flow of the fluid to the delivery ports 40. The inflation lumen 14 terminates at the proximal end of the catheter body and is therefore not shown in FIG. 9.

The inflation and delivery balloons 30, 32 are preferably between 2.0 cm and 6.0 cm in length. However, balloon length can be varied depending upon the requirements of a particular desired application. The deflated profile of the inflation and delivery balloons 30, 32 is preferably between 0.025 inches and 0.070 inches in diameter. The inflation balloon 30 and delivery balloon 32 are sealed, using a process which will be described infra, such that a portion of the distal ends and a portion of the proximal ends of the balloons are sealed together.

The delivery balloon 32 preferably includes a series of discrete delivery ports 40 to enable the delivery of the infused liquid to the desired location. The delivery ports are preferably between 100 $\mu$m and 300 $\mu$m, and more preferably are about 250 $\mu$m in diameter. The discrete delivery ports 40 are preferably disposed radially symmetrically about the outer periphery of the delivery balloon 32 and cover the mid section of the balloon. Depending on the size of the delivery balloon 32 there are preferably 3–50 delivery ports in the delivery balloon 32. Alternatively, fewer delivery ports 40 can be used and disposed only on one hemisphere of the balloon or only the distal end of the balloon, depending on the desired drug delivery pattern.

In the non-perfusion embodiment, due to the relatively large diameter of the delivery ports 40 and the large number of ports 40 on the catheter, the drug slowly drips or "weeps" out of the ports 40. The large number of the large sized delivery ports 40 and the initial low pressure which is used to infuse the drug into the catheter opening results in a very low outlet pressure at the ports 40 of the catheter tip and therefore causes the drug to "weep" out of the ports 40 rather than exiting under a high pressure flow. The "weeping" action causes the drug to exit the catheter tip at a site specific location, however the low pressure delivery of the drug is not enough to penetrate the arterial wall beyond the elastic lamina layer. The delivery of the drug to the artery while maintaining the structural integrity without the penetration of the drug past the laminal wall of the artery will herein be referred to as intraluminal drug delivery, i.e., within the arterial lumen. Further, depending on the use of the catheter, i.e., for PTCA dilatation, for drug delivery or for both operations, the level of inflation of the inflation balloon 30 will influence the drug delivery rate as described infra.

In another embodiment of the non-perfusion catheter, the size of the delivery ports 40 may be reduced to reduce the "weeping" effect and enable a steady flow of the drug to be delivered to the desired vascular site. In a further embodiment, the size of the delivery ports 40 remain the same size as described above and the drug delivery pressure is increased to provide a steady flow of the drug to the desired vascular location. Generally, the total cross sectional area of all ports is at least 300% greater and no more than 400% greater than the cross sectional area of the delivery lumen 16. In a preferred embodiment, the total area of the delivery ports 40 and the pressure of the fluid which is delivered to the vascular site are both varied to achieve the desired delivery profile to the vascular site.

Drug delivery using the non-perfusion embodiment 74 can be performed alone or in combination with a conventional PTCA procedure. When used in combination with a conventional PTCA dilatation operation, the drug may be delivered before, during or after the PTCA procedure. Preferably, the non-perfusion embodiment 74 will be used to deliver thrombolytic agents, such as urokinase, t-PA and the like, when indicated.

When drug delivery is performed before or after conventional PTCA, the inner inflation balloon 30 is inflated or deflated to a relatively low pressure, such as between about 0.4 ATM-1.5 ATM, preferable to about 0.5 ATM. A small luminal channel 79 (See FIG. 9) is maintained between the inner inflation balloon 30 and the outer delivery balloon 32. The luminal channel 79 is typically on the order of approximately 0.01 inches in diameter when the inflation balloon 30 is inflated to a constant 0.5 ATM. Channel 79 permits communication of the drug from delivery lumen 16 to the outer ports 40 in the delivery balloon 32 at an even and continuous rate. As the pressure applied to the drug delivery balloon 32 increases the flow rate out of the ports 40 increases. However, the risk of a sufficiently high pressure to perforate the vascular wall can be minimized by appropriate sizing of the channel 79 with respect to the total cross sectional area of the ports 40 as will be readily understood by one skilled in the art. Drug delivery before the PTCA dilatation may be advantageous as any thrombus which is located near the area to be treated can be dissolved before dilation.

When the inner inflation balloon 30 is inflated to between 2 ATM and 12 ATM, the catheter can be used for dilatation of a stenosis using conventional PTCA techniques. During the PTCA procedure, a drug can also be introduced into the delivery balloon 32 and delivered through the ports 40 to the specific location on the arterial wall. Even during the PTCA procedure, the resultant pressure within the delivery balloon 32 is not enough to deposit the drug into the laminal layer of the arterial wall. Drug delivery during a PTCA procedure may be advantageous to assist in treating the stenosis while the dilatation is occurring. After the PTCA procedure is complete if additional thrombus is discovered, the catheter may be used to deliver medication to the newly discovered thrombus.

Once the drug delivery and or PTCA procedure is complete and the catheter is prepared for extraction from the artery, the pressure is first reduced at the outer delivery balloon 32 to halt continual infusion of the drug during extraction. However, the outer delivery balloon 32 will not immediately collapse. Next, the pressure in the inner inflation balloon 30 is reduced such as by aspiration with the inflation syringe, causing the inner balloon 30 to deflate. The inner and outer balloons 30, 32 are sealed together at both axial ends, as described below, thus the reduction in diameter of the inner balloon 30 reduces the profile of the outer balloon 32.

In the preferred embodiment, at least a portion of the inflation balloon 30 is connected to at least a portion of the delivery balloon 32. This structure permits the inflation balloon to "pull" the delivery balloon with it when the inflation balloon is being aspirated to minimize the external dimensions. The connection between the inflation balloon 30 and delivery balloon 32 can be accomplished in any of a variety of techniques as will be understood by one of ordinary skill in the art.

To provide a relatively small delivery site, the inflation balloon 30 and drug delivery 32 balloon can be heat sealed together along almost the entire axial length of the balloon, leaving only a relatively small unsealed area to allow the delivery of the desired drug. To provide a relatively large delivery site, while maintaining the advantage of "pulling" the delivery balloon 32 in with the inner inflation balloon 30, only the very ends of the inflation balloon 30 and delivery balloon 32 can be sealed together. In addition, as the diameter of the delivery ports 40 increases, the percentage of the axial length of the two balloons 30, 32 that is sealed together must necessarily increases to enable the outer delivery balloon 32 to be "pulled" in by the aspiration of the inner balloon 32, as will be understood by one skilled in the art. Further, as the overall pressure used to aspirate the inner balloon decreases, the percentage of the axial length of the two balloons 30, 32 that is sealed together must also be increased, as will be understood by one skilled in the art.

In the present embodiment, preferably about 25% of the total axial length of the inflation balloon 30 is sealed to the delivery balloon 32 at the proximal end and about 25% of the total axial length of the inflation balloon 30 is sealed to the delivery balloon 32 at the distal end to aid in the deflation process as described above. Desirably, the entire circumference of the distal ends of the inflation 30 and delivery balloons 32 are sealed together. Preferably, a relatively large percentage of the proximal ends of the inflation balloon 30 and delivery balloon 32 are sealed together. The small portion of the two balloons 30, 32 on the proximal end that is not sealed together preferably forms the very small luminal channel 79 between the inflation balloon 30 and the delivery balloon 32.

FIG. 10 illustrates the non-perfusion embodiment 74 of the catheter in communication with a fluid delivery and guidewire entry apparatus 80. A inflation port 82 is provided for the delivery of the inflation fluid to the inflation lumen 14. A delivery port 84 is provided for delivery of the infusion fluid to the delivery lumen 16. Port 86 permits entry of a guidewire into the guidewire lumen 52. Preferably, the guidewire entry port 86 is positioned along the longitudinal axis of the catheter to easily align the guidewire with the guidewire lumen 52 to prevent any unnecessary bending of the guidewire during insertion into the lumen 52. Preferably, the fluid delivery and guide-wire entry apparatus 80 remains outside the patient so the doctor can control the delivery of the fluid and the guidewire from outside the patient's body. In an alternate embodiment, an indeflator (not shown), which is basically a syringe connected to a pressure reading device, is attached to the inflation and delivery ports 82, 84 to monitor the pressure of the fluid which is delivered to the inflation and delivery balloons 30, 32.

Catheters incorporating various features of the present invention can be manufactured in a variety of ways. Some of the preferred manufacturing techniques for catheters of the present invention are discussed below.

The perfusion conduit or temporary stent 18 assembly is manufactured by winding a coil of suitable spring wire, typically having a diameter or thickness dimension in the radial direction of the finished spring of about 0.002 inches. The wire is preferably wound about a mandrel sufficient to produce a spring having a lumen 24 with a diameter of about 0.039 inches.

The coil is preferably provided with an outer sheath or coating, as has previously been discussed. In one embodiment of the method of the present invention, the tightly coiled wire is held securely about the mandrel such as by clamping or soldering each end to the mandrel so that the coil is not permitted to unwind slightly and expand radially following release as will be understood by one of skill in the art. The tightly wound coil is thereafter inserted within a tubular sleeve, such as an extruded non-crosslinked polyethylene tubing of desired size. The spring coil is then released from the mandrel, so that the spring unwinds slightly within the polyethylene tube to produce a tight fit.

Typically, the minimum wall thickness of extruded polyethylene tubing as discussed above is no less than about 0.002 inches. This wall thickness can be reduced by heat stretching the polyethylene tubing either prior to insertion of the spring or directly onto the pre-wound spring coil to provide a tight seal. The heat stretching step of the present invention has been determined to produce a polyethylene coating on the spring coil having a wall thickness as low as about 0.001 inches. Thus, the overall diameter of the stent 18 assembly is reduced by about 0.002 inches.

The body of the catheter may be separately produced, typically by a combination of extrusion and post-extrusion processing steps. For example, an elongate triple lumen triangular cross section catheter body is produced by extrusion of high density polyethylene, to produce a body having a minimum wall thickness within the range of from about 0.003 to about 0.005 inches.

To minimize the overall cross sectional area of the assembled catheter, the distal portion of the tubular body 12 is reduced in diameter and wall thickness such as by axially stretching under the influence of heat. Stretching is accomplished by inserting, in a preferred embodiment, a 0.016 inch diameter pin in the guidewire lumen 52, and a 0.010, inch diameter pin in each of the inflation lumen 14 and drug delivery lumen 16. The distal end of the catheter body is thereafter heat stretched nearly to the limit before breaking. The result of the stretching reduces the cross-section of the triangular catheter body, from base to apex, from about 0.039 inches in the unstretched condition to about 0.025 inches following heat stretching.

The transition zone between the unstretched catheter body 12 and the distal axially stretched portion occurs within about 0.01 inches proximally of the proximal end of the temporary stent 18 in the assembled catheter. It has been determined by the present inventor that the decrease in structural strength of the heat stretched catheter body does not appear to adversely impact the integrity of the assembled catheter, in the designs disclosed herein.

The inflation balloon 30 and drug delivery balloon can be manufactured in any of a variety of manners which are now conventional in the art, such as free-blowing polyethylene, polyethylene terephthalate, nylon, polyester, or any of a variety of other medical grade polymers known for this use. Generally, the interior inflation balloon 30 is produced by blowing relatively long sections of cross-linked polyethylene within a mold to control the outside diameter. The use of cross-linked polyethylene facilitates heat sealing to the coil, which is preferably coated with non-crosslinked polyethylene.

The sections of inflation balloon material are thereafter heat stretched at the proximal and distal necks of a balloon down to a thickness of about 0.001 inches and a diameter which relatively closely fits the portion of the catheter body to which it is to be sealed. The appropriate length is cut, depending upon the desired length of the balloon and balloon necks in the finished catheter.

The proximal neck is heat sealed around the catheter body 12 and the temporary stent 18 as illustrated in FIGS. 1 and 5. In general, the length of the proximal and distal neck which is secured to the catheter body is within the range of from about 0.05 inches to about 0.1 inch, except in an embodiment such as illustrated in FIG. 5, in which the proximal and distal balloon necks are as long as necessary to accomplish their functions as a proximal cover or distal tip. The distal end of the inflation balloon 30 is thereafter heat sealed around the distal end of the temporary stent 18.

The outer balloon may thereafter be assembled in a similar manner, following "necking down" of the axial ends of the balloon by axial stretching under the application of heat. In an embodiment utilizing cross-linked polyethylene for the outer delivery balloon, the delivery balloon is typically secured to the axial ends of the inflation balloon through the use of a UV-curable adhesive, due to the difficulty in thermally bonding cross-linked polyethylene to cross-linked polyethylene.

However, it is to be understood that the material utilized for the outer delivery "balloon" may be varied considerably, and the term "balloon" as used in the context of the delivery balloon is intended to be only generally descriptive of this structure. For example, in addition to perforated balloons, a wide variety of materials not conventionally used for true balloons may also be used. Woven or braided fibers such as dacron, or fluid permeable membranes may desirably be used for the outer delivery balloon, as has been discussed.

In another alternate embodiment of the method and design of the present invention, the cross-sectional configuration of the temporary stent 18 changes from substantially circular at the distal end thereof to substantially rectangular or square at the proximal end thereof. This configuration is accomplished by winding the spring coil around a mandrel having a square cross-sectional portion, a transition portion, and a round cross-sectional portion. The transition portion on the resulting spring is located in the assembled catheter at about the line 4—4 on FIG. 3. This allows the temporary stent portion 18 to retain the same internal cross-sectional area, while reducing the maximum width of the assembled catheter.

Figure 11:
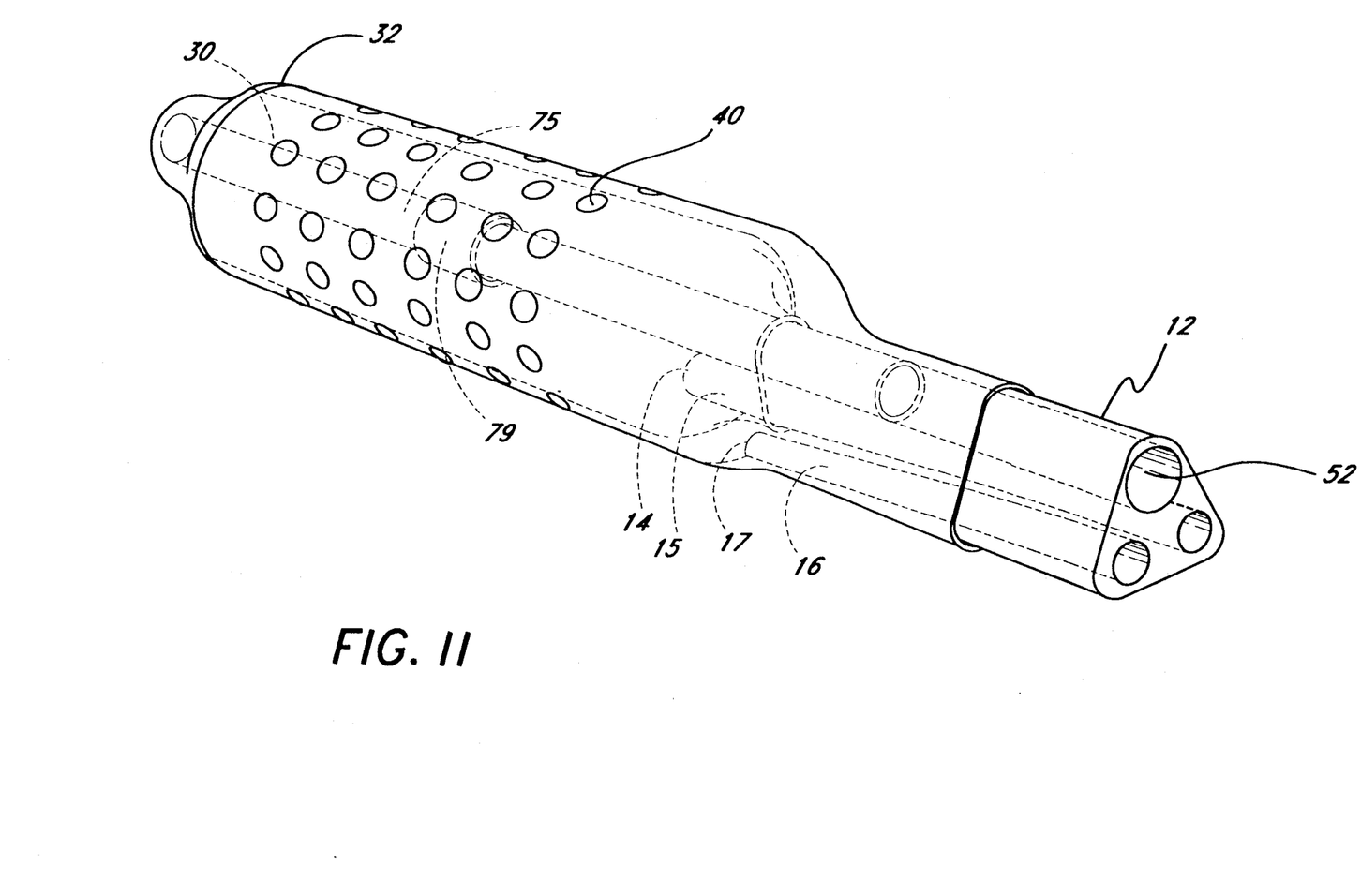
FIG. 11 is a perspective view of the non-stent embodiment of the present invention.

In the non-perfusion embodiment 74, the distal end of the catheter body 12 is cut away to separately expose each of the three lumen as illustrated in FIG. 11. First, a small portion of the catheter body is cut away to expose the drug delivery lumen 16. Next, a larger length is cut away to expose the inflation lumen 14. Finally, an additional portion is cut away to expose the guidewire lumen 52. The central lumen 75 abuts the guidewire lumen and the two lumen are joined together using an adhesive or any other suitable bonding process. A radio opaque marker 76 is preferably positioned in the center of the catheter 74 concentric to the central lumen 75.

A long steel mandrel is inserted into each of the inflation lumen 14, delivery lumen 16, and the guidewire lumen 52 which extends through the central lumen 75, the mandrels extending along the entire length of the catheter body 12. The steel mandrels are provided to keep the lumen from sealing closed during the balloon assembly procedure. The inflation balloon 30 is placed over the central lumen 75 and the inflation lumen 14. The inflation balloon 30 is then bonded to the central lumen 75 and the inflation lumen 14 at the proximal end and to the central lumen 75 at the distal end. The inflation balloon 30 is bonded to the inflation lumen 14 and the central lumen 75 using any of a variety of bonding techniques known to those skilled in the art, such as solvent bonding, thermal adhesive bonding, or by heat sealing. Preferably, in the present invention the inflation balloon 30 is heat sealed to the inflation lumen 14 and the central lumen 75.

Preferably the delivery balloon 32 is bonded to the catheter body 12 by any of a variety of bonding techniques such as solvent bonding, thermal adhesive bonding or by heat sealing depending on the type of balloon material used. In the present invention, crosslinked polyethylene balloons are used, therefore the inflation 30 and delivery balloons 32 are heat sealed together as follows. The wire mandrel is removed from the central lumen 75 and guidewire lumen 52 and a 0.01 inch diameter teflon rod is placed in the central lumen 75 to insure that the central lumen 75 is not sealed closed during the assembly process.

The delivery balloon 32 is positioned at the proximal end of the catheter 74 to cover the inflation balloon 30 and the delivery lumen 16. To create the luminal channel 79, a teflon rod of a diameter which is the same as the desired diameter of the luminal channel 79 is placed between the inflation balloon 30 and the deliver balloon 32 at the proximal end of the two balloons 30, 32. A teflon capture tube (not shown) is positioned over the delivery balloon 32 and covers the portion of the proximal end of the delivery balloon 32 which is to be sealed to the inflation balloon 30. The teflon capture tube is a generally tubular body which has approximately the same diameter as the inflated diameter of the inflation balloon 30 and is made of teflon. The inflation balloon 30 is inflated to a pressure which is sufficient to force the delivery balloon 32 against the wall of the teflon capture tube. Preferably, the inflation balloon 30 is inflated to about 30-50 psi. The capture tube is heated by any of a number of heating means such as electric coils or a furnace to a temperature which is sufficient to bond the two balloons 30, 32 together. In this case, the crosslinked polyethylene balloons are heated to a temperature of about 300° F. which causes both balloons to seal together. The teflon capture tube is then cooled to a temperature below the melting temperature of the two balloons 30, 32. The inflation balloon 30 is deflated and the catheter is removed from the capture tube. The teflon rod used to create the luminal channel 79 is removed.

To seal the distal end of the delivery balloon 32 to the inflation balloon 30, the delivery balloon is positioned at the distal end of the catheter 74 and completely covers the inflation balloon 30. The teflon capture tube (not shown) is positioned over the delivery balloon 32 and covers the portion of the distal end of the delivery balloon 32 which is to be sealed to the inflation balloon 30. The inflation balloon 30 is inflated to force the delivery balloon 32 against the wall of the teflon capture tube. Preferably, the inflation balloon 30 is inflated to about 30-50 psi. As above, the capture tube is heated by any of a number of heating means such as electric coils or a furnace to a temperature which is sufficient to bond the two balloons 30, 32 together. In this case, the crosslinked polyethylene balloons are heated to a temperature of about 300° F. which causes both balloons to seal together. The teflon capture tube is then cooled to a temperature below the melting temperature of the two balloons 30, 32. The inflation balloon 30 is deflated and the catheter is removed from the capture tube. The teflon rod is removed through the distal end of the central lumen 75. The steel mandrels are removed from the inflation lumen 14 and the delivery lumen 16 through the proximal end of the catheter body 12.

In accordance with the method of the present invention, a site is identified in a body lumen where it is desired to deliver an amount of a medication or other gas or fluid. For example, thrombolytic or restenosis inhibiting drugs may be desirably introduced directly to the affected wall following dilatation. Alternatively, anticoagulants, plaque softening agents or other drugs may desirably be delivered directly to the site of a thrombosis or other vascular anomaly.

A conventional angioplasty guidewire is percutaneously transluminally inserted and advanced to the desired treatment site. Guidewires suitable for this purpose are commercially available, having a variety of diameters such as 0.014 inches.

The distal end 22 of temporary stent 18 is threaded over the proximal end of the guidewire once the guidewire has been positioned within the desired delivery site. The catheter 10 is thereafter advanced along the guidewire in the manner of conventional "over-the-wire" balloon angioplasty catheters. A conventional guidewire having an exterior diameter of about 0.014 inches has a cross-sectional area of about 0.000154 inches, and a temporary stent 18 having an interior diameter of about 0.039 inches has an interior cross-sectional area of about 0.001194 inches. The cross-sectional area of the interior lumen 24 of stent 18 which remains available for perfusion once a guidewire is in place is therefore about 0.00104 square inches.

The catheter 10 is advanced through the vascular system, along the guidewire, until the drug delivery balloon 40 is disposed adjacent the desired delivery site. Thereafter, a suitable inflation fluid such as a radiopaque solution is introduced by way of lumen 14 into the inflation balloon 30 to press the delivery balloon 32 against the vascular wall. Although described herein in its drug delivery capacity, the catheter of the present invention may alternatively be used to perform dilatation, as has previously been described.

Once the drug delivery balloon 40 is positioned adjacent the vascular wall, medication is infused by way of lumen 16 in tubular body 12 and expelled through effluent ports 40 directly against the vascular wall. Medication can be introduced under gravity feed alone, or by way of a positive pressure pump, as desired by the clinician in view of such factors as drug viscosity, toxicity and desired delivery time.

In this manner, drugs can be permitted to be absorbed directly into the affected site, with a minimal amount of drug escaping into generalized circulation. The rate of drug delivery is somewhat limited by the rate of absorption by the vascular wall, and delivery rates on the order of about 30 ml per hr. to about 20 ml per minute are presently contemplated for use in the method of the present invention. Certain medications may be optimally delivered at much lower rates, such as 1 ml per day or lower. However, these rates may be modified significantly, depending upon the drug, and the extent to which "overflow" fluid is permitted to escape into the circulatory system.

In the drug delivery application, delivery of a sufficient amount of drug may require an extended period of time. Perfusion past the delivery balloon by way of temporary stent 18 minimizes the adverse impact on circulation due to the indwelling drug delivery catheter. Following infusion of the predetermined volume of drug, and optionally following a further "rinse" with a sufficient volume of N-saline to expel substantially all of the drug from the residual volume of lumen 16 and space between drug delivery balloon 32 and inflation balloon 30, the inflation balloon 30 is deflated and the catheter may be withdrawn.

Alternatively, the catheter 10 can be introduced by way of an introduction sheath having a lumen with a large enough diameter to accommodate catheter 10.

During the foregoing procedures, the guidewire (not illustrated) may either be removed or may be left in place, as will be understood by one of skill in the art. In general, cardiologists prefer to leave the guidewire in place so that the catheter may be withdrawn and replaced, or other catheters may be inserted.

In accordance with a further aspect of the method of the present invention, the catheter 10 is utilized as a temporary stent for an observation period following percutaneous transluminal coronary angioplasty, atherectomy, laser ablation or any of a variety of other interventional catheter techniques and procedures. In an embodiment of the apparatus for use with this aspect of the method of the present invention, the drug delivery balloon 32 may be deleted entirely, and the tubular body 12 may optionally be provided with only a single fluid lumen extending therethrough to provide communication with the interior of inflation balloon 30.

Following removal of an interventional therapeutic catheter, such as an angioplasty, atherectomy or laser ablation catheter, the temporary stent catheter 10 is inserted along the guidewire or through an introduction sheath and disposed with the inflation balloon 30 at the previously treated site. Inflation balloon 30 is inflated to the desired diameter to resist reocclusion during a post-procedure period. Such observation periods may vary depending upon the circumstances of the patient and the cardiologist, but generally range from about 30 minutes to about 24 hours. During this time, perfusion across the inflation balloon 30 is permitted by way of temporary stent 18.

As has been previously described, the relative cross-sectional area of the lumen 24, even with an indwelling guidewire, permits a significant degree of perfusion to occur. In addition, the longitudinal axis of lumen 24 is generally concentric with or parallel to the longitudinal axis of the artery or vein in which the indwelling temporary stent is disposed. In this manner, the interruption of direction of blood flow is minimized, thereby reducing the likelihood of damaging blood cells and introducing undesired turbulence.

Although this invention has been described in terms of certain preferred embodiments, other embodiments that are apparent to those of ordinary skill in the art are also within the scope of the invention. Accordingly, the scope of the invention is intended to be defined only by reference to the appended claims.

What is claimed:

1. A drug delivery and balloon dilatation catheter, comprising:
    an elongate catheter body, having proximal and distal ends;
    an inflation balloon on the distal end of the catheter body, the inflated profile of said inflation balloon having proximal and distal conical sections and a central cylindrical section,
    a delivery balloon on the catheter, disposed about the inflation balloon;
    a first lumen extending through the catheter for communication with the inflation balloon;
    a second lumen extending through the catheter for communication with the delivery balloon;
    a proximal annular seal between the inflation balloon and the delivery balloon; and
    a distal annular seal between the inflation balloon and the delivery balloon;
    wherein said proximal and distal annular seals extend axially into the conical sections of the inflation balloon so that deflation of the inflation balloon will cause a reduction in the exterior profile of the delivery balloon.

2. A delivery catheter as in claim 1, wherein said inflation balloon comprises polyethylene.

3. A delivery catheter as in claim 2, wherein said delivery balloon comprises polyethylene.

4. A delivery catheter as in claim 1, wherein the sum of the axial lengths of the proximal and distal annular seals in within the range of from about 10% to about 60% of the axial length of the delivery balloon.

5. A delivery catheter as in claim 4, wherein at least one of said proximal and distal annular seals extends for approximately 25% of the axial length of the delivery balloon.

6. A delivery catheter as in claim 1, wherein said delivery balloon comprises a plurality of delivery ports.

7. A delivery catheter as in claim 6, wherein said delivery ports are between about 100 microns and about 300 microns in diameter.

8. A delivery catheter as in claim 7, wherein said delivery ports are preferably about 250 microns in diameter.

9. A delivery catheter as in claim 6, wherein the total cross-sectional area of all of said delivery ports is at least 300% of the cross-sectional area of the second lumen.

10. A delivery catheter as in claim 1, wherein said delivery balloon comprises between about 3 and 50 delivery ports.

11. A delivery catheter as in claim 1, further comprising a delivery passageway extending through said proximal annular seal to provide communication between the second lumen and the delivery balloon.

12. A delivery catheter as in claim 1, wherein the deflated profile of the delivery balloon is preferably between 0.025 inches and 0.070 inches in diameter.

13. A delivery and balloon dilatation catheter for delivering a quantity of a fluid to a preselected site in a body lumen, comprising:
    an elongate catheter body having proximal and distal ends;
    a cross linked polyethylene inflation balloon on the distal end of the catheter body the inflated profile of said inflation balloon having proximal and distal control sections and a central cylindrical section;

a delivery balloon on the catheter, disposed coaxially about the inflation balloon;

a first lumen extending through the catheter for communication with the inflation balloon;

a second lumen extending through the catheter for communication with the delivery balloon;

a first annular seal between the distal end of the inflation balloon and the delivery balloon, said first annular seal extending axially into the cylindrical section of the inflation balloon;

a second annular seal between the proximal end of the inflation balloon and the delivery balloon, said second annular seal extending axially into the cylindrical section of the inflation balloon; and a delivery passageway extending through said second annular seal to provide communication between the second lumen and the delivery balloon;

wherein deflation of the inflation balloon will cause a reduction in the exterior profile of the delivery balloon.

14. A delivery catheter as in claim 13, wherein from about 10% to 60% of the axial length of the delivery balloon is bonded to the inflation balloon.

15. A delivery catheter as in claim 14, wherein said first annular seal extends approximately 25% of the axial length of the delivery balloon.

16. A delivery catheter as in claim 14, wherein said second annular seal extends approximately 25% of the axial length of the delivery balloon.

17. A delivery catheter as in claim 13, further comprising a wire receiving lumen extending throughout at least a portion of the axial length of the catheter, wherein the longitudinal axis of the wire receiving lumen is co-axial to the inflation balloon on the distal end of the catheter body.

18. A delivery catheter as in claim 13, wherein said delivery balloon comprises a plurality of delivery ports.

19. A delivery catheter as in claim 18, wherein said delivery ports are between about 100 μm and about 300 μm in diameter.

20. A delivery catheter as in claim 19, wherein said delivery ports are preferably about 250 μm in diameter.

21. A delivery catheter as in claim 18, wherein said delivery balloon comprises between about 3 and 50 delivery ports.

22. A delivery catheter as in claim 13, wherein a majority of the length of said catheter body has a cross sectional area which i generally triangular in shape.

23. A delivery catheter as in claim 13, wherein said fluid is delivered intraluminally.

* * * * *